United States Patent
Bordet et al.

(10) Patent No.: US 9,045,393 B2
(45) Date of Patent: *Jun. 2, 2015

(54) DERIVATIVES OF 3.5-SECO-4-NORCHOLESTANE AND USE THEREOF

(75) Inventors: Thierry Bordet, Paris (FR); Cyrille Drouot, Draguignan (FR)

(73) Assignee: TROPHOS (FR)

( * ) Notice: Subject to any disclaimer, the term of this patent is extended or adjusted under 35 U.S.C. 154(b) by 1488 days.

This patent is subject to a terminal disclaimer.

(21) Appl. No.: 11/662,088

(22) PCT Filed: Aug. 19, 2005

(86) PCT No.: PCT/FR2005/002116
§ 371 (c)(1),
(2), (4) Date: Feb. 26, 2008

(87) PCT Pub. No.: WO2006/027454
PCT Pub. Date: Mar. 16, 2006

(65) Prior Publication Data
US 2008/0275130 A1 Nov. 6, 2008

(30) Foreign Application Priority Data

Sep. 7, 2004 (FR) ..................... 04 09436

(51) Int. Cl.
*A61K 31/15* (2006.01)
*C07C 251/44* (2006.01)

(52) U.S. Cl.
CPC ........... *C07C 251/44* (2013.01); *C07C 2103/12* (2013.01)

(58) Field of Classification Search
CPC .................. C07C 251/44; C07C 2103/12
USPC .......................................... 514/640; 564/267
See application file for complete search history.

(56) References Cited

U.S. PATENT DOCUMENTS

| | | | |
|---|---|---|---|
| 2,883,424 | A | 4/1959 | Wildi |
| 7,858,603 | B2 | 12/2010 | Bordet et al. |
| 7,985,774 | B2 | 7/2011 | Pruss et al. |
| 2008/0275130 | A1 | 11/2008 | Bordet et al. |
| 2009/0186863 | A1 | 7/2009 | Pruss et al. |
| 2009/0203662 | A1 | 8/2009 | Drouot et al. |
| 2010/0099652 | A1 | 4/2010 | Drouot et al. |
| 2010/0216752 | A1 | 8/2010 | Bordet et al. |
| 2010/0267680 | A1 | 10/2010 | Pruss et al. |
| 2010/0267837 | A1 | 10/2010 | Pruss et al. |
| 2010/0310674 | A1 | 12/2010 | Pruss et al. |
| 2011/0224180 | A1 | 9/2011 | Pruss et al. |
| 2011/0275680 | A1 | 11/2011 | Drouot et al. |

FOREIGN PATENT DOCUMENTS

| | | |
|---|---|---|
| WO | WO 97/02027 | 1/1997 |
| WO | WO 03/007933 | 1/2003 |

OTHER PUBLICATIONS

Brunke et al., "Synthesis of (+_)-20-methylpregn-4-en-3-one and (+_)-20-methyl-14beta,17alpha-pregn-4-en-3-ne via ionic cyclization of a tetraenol with preformed "ring C".", Chemische Berichte, vol. 113, No. 8, pp. 2714-2728, 1980 (English Abstract only).*
Singh et al., "Steroids and related studies. L. Thin-layer chromatography of some steroidal ketones, oximes, amides, lactams and tetrazoles". J. of Chromatography, vol. 176 No. 2, pp. 255-259, 1979 (English Abstract only).*
Jones et al., "Steroidal sulfur compounds. XI. 4-Thia-5alpha- and -5beta-cholestane and their oxides and dioxides"., J. of the Chemical Society, Perkin Trans. 1: Organic and Bio-organic Chemistry, No. 23, pp. 2637-2645, 1974.*
Uusvuori et al., "Oxidation of cyclic hemiacetals into diketones: final steps in the conversion of a triterpenoid ring A into a steroidal enone by a new short route." Synthetic Communications, vol. 12(14), pp. 1081-1088, 1982. English Abstract attached.*
Pradhan et al., "Unusual reactions of steroidal and non-steroidal 1,5-dioximes. Stereochemistry and mechanism of formation of N-hydroxypiperidine analogs." Heterocycles, vol. 28(2), pp. 813-839, 1989. English Abstract.*
Becker, et al., "Stilbazulenyl Nitrone (STAZN): A Nitronyl-Substituted Hydrocarbon with the Potency of Classical Phenolic Chain-Breaking Antioxidants", *J. Am. Chem. Soc.*, vol. 124, pp. 4678-4684, 2002.
Camu, et al., "Purification of Spinal Motoneurons from Chicken and Rat Embryos by Immunopanning", *Neuroprotocols: A Companion to Methods in Neurosciences*, vol. 2, pp. 191-199, 1993.
Casanovas, et al., "Prevention by Lamotrigine, MK-801 and $N_w$-Nitro-$_L$-Arginine Methyl Ester of Motoneuron Cell Death After Neonatal Axotomy", *Neuroscience*, vol. 71, No. 2, pp. 313-325, 1996.
Field, et al., "Detection of static and dynamic components of mechanical allodynia in rat models of neuropathic pain: are they signalled by distinct primary sensory neurones?", *Pain*, vol. 83, pp. 303-311, 1999.
Field, et al., "Gabapentin and pregabalin, but not morphine and amitriptyline, block both static and dynamic components of mechanical allodynia induced by streptozocin in the rat", *Pain*, vol. 80, pp. 391-398, 1999.
Fleming, et al., "Behavioral Effects of Dopaminergic Agonists in Transgenic Mice Overexpresing Human Wildtype α-Synuclein", *Neuroscience*, vol. 142(4), pp. 1245-1253, 2006.
Fleming, at al., "Early and Progressive Sensorimotor Anomalies in Mice Overexpressing Wild-Type Human α-Synuclein", *Neurobiology of Disease*, vol. 24(42), pp. 9434-9440, Oct. 20, 2004.

(Continued)

*Primary Examiner* — Barbara P Badio
(74) *Attorney, Agent, or Firm* — Browdy and Neimark, PLLC

(57) ABSTRACT

The invention relates to compounds of formula (I): where X+Y=keto, or X=OH and Y=H, or X+Y=oxime or methyloxime, B=OH and C+D=H, or C+D=C1-C4 linear or branched alkyl, or C=H and D=C1-C4 linear or branched alkyl, or B+C=keto and D=methyl, hydroxyl, or methylamino, or B and C=H and D=methylamino, or B+C=oxime and D=methyl and R=C1-C10 linear or branched alkyl, the salts, esters, or salts of esters thereof as medicament, in particular as neuroprotectors, novel compounds of formula (I) and pharmaceutical compositions.

25 Claims, No Drawings

(56) References Cited

OTHER PUBLICATIONS

Fleming, et al., "Olfactory deficits in mice overexpressing human wildtype α-synuclein", *Eur. J. Neurosci.*, vol. 28(2), pp. 247-256, 2008.

Henderson, et al., "Neurotrophins promote motor neuron survival and are present in embryonic limb bud", *Nature*, vol. 363, pp. 266-270, May 20, 1993.

Malcangio, et al., "A pharmacologic analysis of mechanical hyperalgesia in streptozotocin/diabetic rats", *Pain*, vol. 76, pp. 151-157, 1998.

Novelli, et al., "Phenyl-T-Buryl-Nitrone Is Active Against Traumatic Shock in Rats", *Free Rad. Res. Comms.*, vol. 1, No. 5, pp. 321-327, 1985.

Oksman, et al., "Behavioural and neurochemical response of α-synuclein a30P transgenic mice to the effects of L-Dopa", *Neuropharmacology*, vol. 56, pp. 647-652, 2009.

Pettmann, al., "Neuronal Cell Death", *Neuron*, vol. 20, pp. 633-647, Apr. 1998.

Richter, et al., Abstract, "The cholesterol-oximes TRO19622 and TRO40303 affect motor function, olfaction, and alpha synuclein aggregation in mice overexpressing human alpha synuclein under the Thy1 promoter", *Society for Neuroscience Annual Meeting*, 750.28, 2010.

Scadding, et al., "Painful peripheral neuropathies", *Wall and Melzack's Textbook of Pain*, 5$^{th}$ Edition, Chapter 62, pp. 973-999, 2006.

Standaert, et al., "Treatment of Central Nervous System Degenerative Disorders", *The Pharmacological Basis of Therapeutics*, eleventh edition, chaper 20, pp. 527-545, 2006.

Tofaris, et al., "Physiological and pathological properties of α-synuclein", *Cellular and Molecular Life Sciences*, vol. 64, pp. 2194-2201, 2007.

Yuan, et al., "Apoptosis in the nervous system", *Nature*, vol. 407, pp. 802-809, Oct. 12, 2000.

\* cited by examiner

DERIVATIVES OF 3,5-SECO-4-NORCHOLESTANE AND USE THEREOF

The present invention relates to the application as drugs, of derivatives of 3,5-seco-4-nor-cholestane, notably as neuroprotectives for example in pathologies and traumas related to degeneration or death of motoneurons, to pharmaceutical compositions containing them, to novel derivatives and to their method of preparation.

Neurodegenerative processes are characterized by dysfunction and death of neurons causing the loss of neurological functions mediated by the brain (central nervous system, CNS), the spinal cord and the peripheral nervous system (PNS). They may result i.a. from pathological situations grouped under the term of neurodegenerative diseases or affections, from trauma or exposure to toxins.

The most important pathologies which are characterized by a degenerative process are:
- neurodegenerative, hereditary or sporadic chronic diseases, notably Alzheimer's disease, Huntington's disease, Parkinson's disease, amyotrophic lateral sclerosis, spinal amyotrophies, Creutzfeldt-Jakob disease, multiple sclerosis, adrenoleucodystrophy, epilepsy, dementias, schizophrenia, and neurological syndromes associated with AIDS;
- neuronal lesions related to ageing;
- hereditary or lesional peripheral neuropathies, such as Fabry's, Charcot-Marie-Tooth's, Krabbe's diseases, leucodystrophies, diabetic neuropathies, and those induced by anti-cancer treatments;
- traumas of the brain, of peripheral nerves and of the spinal cord;
- ischemias of the brain or spinal cord as a result of a cerebrovascular stroke, or induced by a lack of blood irrigation;
- hereditary, lesional degenerations, or those related to ageing of the sensory neurons of vision, such as macular degenerations, pigmentary retinitis or degenerations of the optical nerve induced by glaucomas;
- traumatic, hereditary degenerations or those related to ageing of sensory neurons of audition causing impairment or loss of audition.

A portion of the signaling routes affected in these pathologies are common to a large number of neurodegenerative diseases. Alzheimer's disease is the most frequent dementia. It causes the apparition of an atrophy of the brain, a predominant loss of neurons in Ammon's horm and it also affects cholinergic neurons. Other pathologies, such as lobar atrophies (Pick's disease, Creutzfeldt-Jakob disease, Lewy's body dementia, vascular dementias, Parkinson's disease are associated with significant neuronal death at the origin of the symptoms of these dementias.

Presently, there is no effective treatment for stopping neuronal degenerations. A therapeutical approach for protecting neurons against death is providing neurotrophic proteins.

These proteins, such as BDNF (brain-derived neurotrophic factor), CNTF (ciliary neurotrophic factor), NGF (nerve growth factor), GDNF (glia-derived neurotrophic factor), are synthesized during embryo development or after a lesion in adults. These growth factors promote survival, maturation and differentiation of neuronal cells. Further, they inhibit apoptotic mechanisms, activate multiple survival routes and protect a large number of neuronal populations. Their use is proposed in most neuronal degenerations.

Compounds which would activate expression of neurotrophic factors or which would mimic the action of these factors have therapeutical potential for treating neurodegenerative syndromes.

In particular, providing neurotrophic molecules for treating neuronal degenerations aims at three goals;
- compensate a potential lack of neurotrophic factors related to a lack of supply from peripheral or central targets of the neurons and/or a disorder of the retrograde transport of these factors;
- intervene in a non-specific way on biochemical routes involved in the degenerative cascade;
- promote natural phenomena compensating dendritic growth and arborization of nerve endings.

These compounds would therefore have a beneficial effect on a large number of pathologies, in particular in pathologies affecting the central and peripheral nervous systems.

Moreover, within the scope above, motoneurons are neurons notably present in the spinal cord and brain stem. Their degeneration or their death may lead to gradual weakening of the muscles of the limbs, and then to atrophy and possibly to spasticity (i.e. permanent contraction) of the muscle.

The most important pathologies which result from degeneration and death of spinal and/or bulbar motoneurons are amyotrophic lateral sclerosis, also known as Charcot's disease or further as Lou Gehrig's disease, and infantile spinal amyotrophies, also known as Werdnig-Hoffmann's disease or Kugelberg-Welander's disease.

Further, degeneration of the motoneurons is observed in the case of traumas with crushing and/or sectioning of the spinal cord or of the peripheral motor nerves.

More generally, one speaks of spinal amyotrophies for diseases in which degeneration or death of motoneurons of the spinal cord are involved.

Amyotrophic Lateral Sclerosis (ALS) is a neurodegenerative disease associated with different types of inclusions such as Lewy's bodies and characterized by degeneration of spinal and cortical motoneurons, the fatal outcome of which is sometimes associated with frontal dementia. During development of ALS, degenerative phenomena occur not only in the brain but also in the spinal cord and accordingly in the muscle, through lack of innervation.

Active compounds are always sought for controlling the ailments mentioned above.

Now, the applicant has discovered that derivatives of 3,5-seco-4-nor-cholestane and notably 3,5-seco-4-nor-cholestan-5-one oxime-3-ol were endowed with remarkable neuroprotective properties, particularly with regard to motoneurons, neurons of the central nervous system, of the motor and peripheral nerves, and were therefore useful as drugs.

This is why the present invention concerns compounds described by formula I

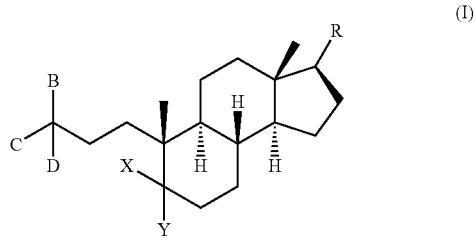

wherein
X represents together with Y a keto function, or X represents a hydroxyl and Y a hydrogen, or X and Y together represent an oxime (=NOH) or a methyloxime (=NHOMe), B represents a hydroxyl and C and D represent a hydrogen, or C and D represent linear or branched alkyls with 1 to 4 carbon atoms, or C represents a hydrogen and D a linear or branched alkyl with 1 to 4 carbon atoms, or else B represents together with C a keto function and D a methyl, hydroxyl or methylamine or else B and C represent a hydrogen and D a methylamine, or else B and C together represent an oxime and D a methyl, and R represents a linear or branched alkyl with 1 to 10 carbon atoms, their esters, as well as their addition salts with pharmaceutically acceptable acids, for their use in a therapeutical method for treating the human or animal body, i.e., as drugs.

The addition salts with pharmaceutically acceptable acids may for example be salts formed with hydrochloric, hydrobromic, nitric, sulfuric, phosphoric, acetic, formic, propionic, benzoic, maleic, fumaric, succinic, tartaric, citric, oxalic, glyoxylic, aspartic, alkane-sulfonic acids, such as methane- or ethane-sulfonic acids, arylsulfonic acids, such as benzene- or paratoluene-sulfonic acids, or carboxylic acids.

As is understood by one skilled in the art, a certain number of compounds of formula I which comprise one or more hydroxyl groups may be esterified. These esters as well as their addition salts with pharmaceutically acceptable acids are not generally directly active per se but they form prodrugs for the corresponding hydroxylated analogs. These esters, which are metabolized in the human organism, lead to the active compounds. These esters are also the object of the present invention. Esters introducing chemical functionalities, such as sulfates, phosphates, acids and basic chains which increase water solubility and bioavailability, may be mentioned. Esters of compounds bearing a basic function are preferred such as the analogs of dialkylglycine with alkyls of 1 to 4 carbon atoms and most particularly dimethylglycine and diethylglycine and also methylpiperazine.

In the present application and in the following, the term "linear or branched alkyl with 1 to 4 carbon atoms" for example designates a methyl, ethyl, propyl, isopropyl, preferably a methyl or ethyl and particularly a methyl.

The term "linear or branched alkyl with 1 to 10 carbon atoms" for example designates a 2-methyl-3-ethyl-heptane, 3-ethyl-heptane, 3-methyl-heptane, preferably 2-ethyl-heptane and particularly 2-methyl-heptane radical of cholestane, as illustrated below

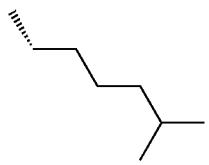

Therefore, the compounds of formula

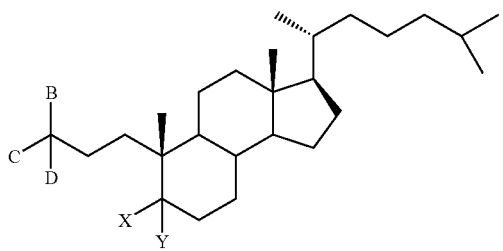

wherein B, C, D, X and Y have the meaning already indicated, are more particularly retained.

Among the compounds of formula I described above, compounds of formula I are notably retained, for which X represents together with Y a keto function, as well as their esters and addition salts with pharmaceutically acceptable acids.

The above compounds are more particularly retained, those for which

B represents a hydroxyl and C and D represent a hydrogen, or C and D representing 2 linear or branched alkyls with 1 to 4 carbon atoms, B represents together with C a keto function and D represents a methyl, as well as their esters and addition salts with pharmaceutically acceptable acids.

Among the compounds of formula I described above, compounds of formula I are notably retained, those for which X and Y represent together an oxime, as well as their esters and addition salts with pharmaceutically acceptable acids.

More particularly the above compounds are retained, those for which

B represents together with C a keto function and D represents a methyl, hydroxyl, methylamine, B represents a hydroxyl, and C and D represent a hydrogen, or C and D represent 2 linear or branched alkyls with 1 to 4 carbon atoms, or C represents a hydrogen and D a linear or branched alkyl with 1 to 4 carbon atoms, B and C represent a hydrogen and D a methyl amine.

B together with C represents an oxime and D represents a methyl, as well as their esters and their addition salts with pharmaceutically acceptable acids.

Most particularly 3,5-seco-4-nor-cholestan-5-one oxime-3-ol, 3,5-seco-4-nor-cholestan-5-one oxime-3-methyl alcohol, 3,5-seco-4-nor-cholestan-5-one oxime-3-dimethyl alcohol, are retained as well as their esters and their addition salts with pharmaceutically acceptable acids.

Addition salts with pharmaceutically acceptable acids of the compounds of formula I or families of the above compounds, their esters and addition salts with pharmaceutically acceptable acids of said esters are thereby particularly retained.

The compounds, object of the present invention, have very interesting pharmacological properties. They are notably endowed with remarkable neuroprotective properties, particularly with regard to motoneurons.

These properties are illustrated in the experimental part hereafter. They justify the use of the compounds described above as well as of their addition salts with pharmaceutically acceptable acids, as a drug.

The drugs according to the present invention find their use because of their neuroprotective properties for example in treating or preventing neurodegenerative affections, such as for example Huntington's disease, neurodegenerative, hereditary or sporadic chronic diseases, neuronal lesions related to ageing, hereditary or lesional peripheral neuropathies, Charcot-Marie-Tooth's disease, diabetic neuropathies or those induced by anti-cancer treatments, traumas of the brain, of the peripheral nerves or of the spinal cord, ischemias of the brain or spinal cord, hereditary, lesional degenerations or those related to ageing of the sensory neurons of vision or degenerations of the optical nerve, the hereditary, traumatic degenerations or those related to the ageing of sensory neurons of audition, lobar atrophies and vascular dementias and notably spinal amyotrophies, amyotrophic lateral sclerosis and pathologies due to traumas of the spinal cord or of the peripheral motor nerves.

In the context of the invention, the term "treatment" designates the preventive, curative, palliative treatment, as well as patient management (reduction of suffering, improving life span, slowing down progression of the disease), etc. The treatment may further be carried out in combination with other ingredients or treatments, such as notably other active compounds for treating the pathologies or traumas specified in the present application.

Because of their neuroprotective properties with regard to motoneurons, they notably find their use, in particular in treating spinal amyotrophies, notably amyotrophic lateral sclerosis or infantile spinal amyotrophies, and in treating traumas of the spinal cord or of the peripheral motor nerves, as mentioned above.

Generally, the daily dose of the compound will be the minimum dose for obtaining the therapeutical effect. This dose will depend on different factors as mentioned earlier. The doses of the above described compounds and for example of 3,5-seco-4-nor-cholestan-5-one oxime-3-ol will generally be between 0.001 to 100 mg per kilo by day for humans.

If necessary, the daily dose may be administered in two, three, four, five, six, or more takings per day or by multiple sub-doses administered per suitable intervals during the day.

The selected amount will depend on multiple factors, in particular on the administration route, on the administration period, on the administration instant, on the elimination rate of the compound, on the different product(s) used in combination with the compound, on the age, on the weight, and on the physical condition of the patient, as well as on his/her medical history, and on any other information known in medicine.

The prescription of the attending physician may begin with doses less than those generally used, and these doses will then be gradually increased so as to better control the occurrence of possible side effects.

The invention also relates to pharmaceutical compositions which contain at least one aforementioned compound or one of its addition salts with pharmaceutically acceptable acids, as an active ingredient.

In these compositions, the active ingredient is advantageously present at a physiologically efficient dosage; the aforementioned compositions notably contain an effective neuroprotective dose of at least one above active ingredient.

As drugs, the compounds described by formula I, their esters, their addition salts with pharmaceutically acceptable acids as well as the addition salts with pharmaceutically acceptable acids of said esters, may be incorporated into the pharmaceutical compositions intended for the digestive or parenteral route.

The pharmaceutical compositions according to the invention may further comprise at least one other therapeutically active ingredient, for a simultaneous, separate or time-spread use, notably during a treatment of a subject affected with a pathology or a trauma related to the degeneration or death of motoneurons as defined above.

The pharmaceutical compositions or drugs according to the invention advantageously comprise one or more inert excipients or carriers, i.e., pharmaceutically inactive and nontoxic. For example, saline, physiological, isotonic, buffered solutions, etc. compatible with pharmaceutical use and known to one skilled in the art, may be mentioned.

The compositions may contain one or more agents or carriers selected from dispersants, solubilizers, stabilizers, preservatives, etc. Agents or vehicles which may be used in formulations (liquid and/or injectable solid formulations) are notably methylcellulose, hydroxymethyl-cellulose, carboxymethylcellulose, cyclodextrins, polysorbate 80, mannitol, gelatin, lactose, vegetable or animal oils, acacia, etc. The compositions may be formulated as an injectable suspension, as gels, oils, tablets, suppositories, powders, gelatin capsules, capsules, etc., optionally by means of dosage forms or devices providing sustained and/or delayed release. For this type of formulation, an agent such as cellulose, carbonates or starches, is used advantageously.

Administration may be achieved by any method known to one skilled in the art, preferably via an oral route or by injection, typically via an intraperitoneal, intracerebral, intrathecal, intravenous, intra-arterial, or intramuscular route. Oral administration is preferred. As this is a long term treatment, the preferred administration route will be sublingual, oral or transcutaneous.

For injections, the compounds are generally conditioned as liquid suspensions, which may be injected by means of syringes or by infusions, for example. It is understood that the flow rate and/or the injected dose or generally the dose to be administered, may be adapted by one skilled in the art according to the patient, the pathology, the mode of administration, etc. It is understood that repeated administrations may be performed, optionally in combination with other active ingredients or any pharmaceutically acceptable carrier (buffers, saline, isotonic solutions, in the presence of stabilizers, etc.).

The invention may be used in mammals, notably in humans.

The object of the present invention is further a method for preparing a composition as described above, characterized in that the active ingredient(s) are mixed according to methods known per se, with acceptable excipients, notably pharmaceutically acceptable excipients.

The compounds of formula I as defined above are known or may be prepared according to methods described in the literature. Certain derivatives of formula I are novel products.

This is why the object of the present application is also novel compounds described by formula I

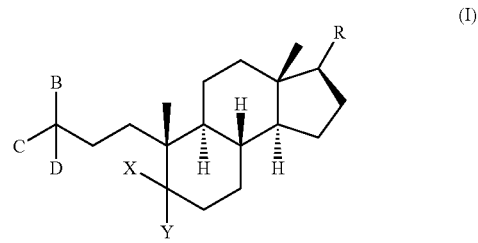

wherein
- X and Y represent together an oxime, B and C represent a hydrogen, C represents a hydrogen and D a methylamine,
- X represents together with Y a keto function, B represents a hydroxyl, and C and D represent methyls,
- X and Y together represent an oxime, B represents a hydroxyl, and C and D represent methyls,
- X and Y together represent an oxime, B represents a hydroxyl, C represents a hydrogen and D represents a methyl,
- X and Y together represent the methyloxime group, B represents a hydroxyl and C and D represent hydrogens, as well as their addition salts with mineral or organic acids.

The object of the present invention is also a method for preparing novel compounds of formula I as defined above as well as their salts, characterized in that a compound of formula II is reacted,

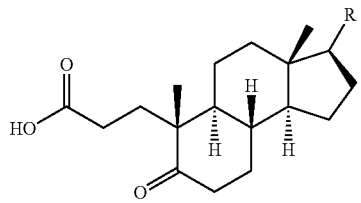
(II)

wherein R represents a linear or branched alkyl with 1 to 10 carbon atoms, which is submitted either to the action of methylamine and then hydroxylamine in order to obtain a compound of formula I wherein R has the meaning already indicated, X and Y represent together an oxime, B represents together with C a keto function and D a methylamine or to methylation in order to obtain a compound of formula III

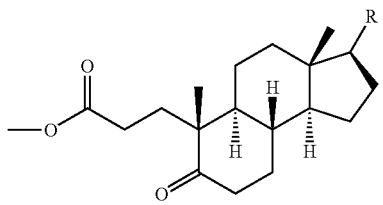
(III)

wherein R has the meaning already indicated, which is submitted to the action of an agent protecting the ketone function in position 5 in order to obtain a compound of formula IV

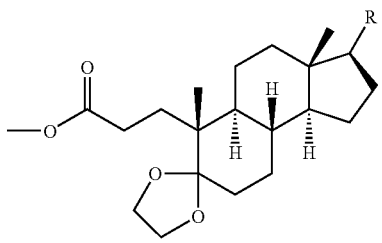
(IV)

wherein R has the meaning already indicated, which or else is reacted with methyl lithium and then submitted to the action of an agent deprotecting the ketone function in position 5 and then reacted with hydroxylamine in order to obtain a compound of formula I wherein R has the meaning already indicated, X and Y represent together an oxime, B represents a hydroxyl and C and D represent linear or branched alkyls with 1 to 4 carbon atoms, or else it is saponified, and then reacted with a compound of formula $H_3C-NH-OCH_3$, and then reacted with methyl lithium, in order to obtain a compound of formula V

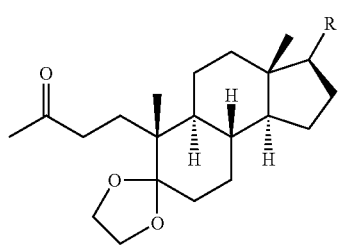
(V)

which is submitted to reduction of the ketone function and then submitted to an agent for deprotecting the ketone function in position 5 and then reacted with hydroxylamine in order to obtain a compound of formula I, wherein R has the meaning already indicated, X and Y represent together an oxime, B represents a hydroxyl, and C represents an optionally substituted linear or branched alkyl with 1 to 4 carbon atoms and D represents a hydrogen, or else it is reduced in order to obtain a compound of formula VI

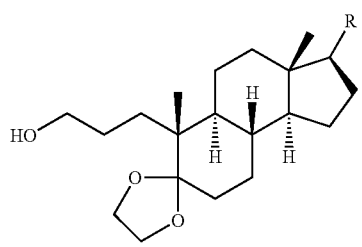
(VI)

wherein R has the meaning already indicated, B represents a hydroxyl, and C and D represent a hydrogen, which, either is submitted to the action of an oxidation agent in order to obtain a compound of formula VII

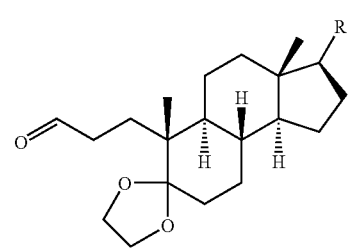
(VII)

wherein R has the meaning already indicated, Schiff's base of which is prepared and then reduced, and then is submitted to the action of an agent for deprotecting the ketone function in position 5, and then is reacted with hydroxylamine in order to obtain a compound of formula I wherein R has the meaning already indicated, X and Y represent together an oxime, B represents a methylamine and C and D represent a hydrogen, or is submitted to the action of an agent for deprotecting the ketone function in position 5, and then is reacted with an amine selected from hydroxylamine, methylhydroxylamine and carboxymethylhydroxylamine in order to obtain a compound of formula I wherein R has the meaning already indicated, X and Y represent together an oxime, a methyloxime, and a carboxymethyloxime respectively, B represents a hydroxyl, and C and D represent a hydrogen, and the compounds of formula I are isolated and if desired, salified or the compounds of formula I are then esterified, if desired.

Under the preferential conditions for applying the method described above, the reaction of the compound of formula II with methylamine is conducted in the presence of a coupling agent activating the acid function such as BOP (benzotriazol-1-yl-oxy-tris-(dimethylamino)-phosphonium hexafluorophosphate) or TBTU (2-(1H-benzotriazol-1-yl)-1,1,3,3-tetramethyluronium tetrafluoroborate) advantageously in the presence of a base such as N-methylmorpholine, notably in a suitable solvent such as dichloromethane or dimethylformamide. Preferably, it is conducted in the presence of EDCI (1-ethyl-3-(3'-dimethylaminopropyl)-carbodiimide) associated with 4-dimethylaminopyridine in dichloromethane, the mixture being submitted to stirring at room temperature for 24 hrs. The product is then put into a solution, preferably in pyridine, and 5 to 7 and notably 6 equivalents of hydroxylamine hydrochloride are then added.

Methylation of the compound of formula II is achieved by reaction with methanol in the presence of thionyl chloride, preferably by solubilizing the acid of formula II in a suitable volume of a 70% methanol and 30% dichloromethane mixture. It is cooled to 0° C. and 3 equivalents of thionyl chloride are added dropwise. It is then stirred for 2 hrs at room temperature.

On this compound, protection of the ketone function is preferably carried out by solubilizing the product in an excess, for example 10 equivalents, of trimethyl orthoformate and a sufficient volume of ethylene glycol, and then by adding anhydrous p-toluenesulfonic acid.

The reaction of the compound of formula IV with methyl lithium is preferably carried out in anhydrous THF, and then after cooling to about −45° C., dropwise addition of an excess of methyl lithium.

Deprotection of the dioxolane which blocks the ketone function in position 5, is achieved in acetone in the presence of sulfuric acid. Preferably, this is achieved in dioxane in the presence of a water/acetic acid 1/1 mixture. The oxime of the ketone is advantageously produced as above.

Saponification of the compound of formula IV is achieved with soda, preferably in dioxane. About 2 equivalents of an aqueous soda solution are notably added.

This product is reacted with a compound of formula $H_3C$—NH—$OCH_3$ for example in the presence of a coupling agent activating the acid function such as BOP or TBTU in the presence of a base such as N-methylmorpholine in a suitable solvent such as dichloromethane or dimethylformamide. Preferably, this is accomplished in the presence of EDCI associated with hydroxybenzotriazole with triethylamine being added dropwise into the solvent.

This product is reacted with methyl lithium under an argon atmosphere according to the procedure described above, and the ketone function in position 3 is then reduced by sodium borohydride.

The obtained product is then submitted to deprotection of the ketone function in position 5 and reacted with hydroxylamine according to the same procedure as described above.

Reduction of the compound of formula IV in order to obtain the compound of formula VI is preferably achieved with aluminum lithium hydride, notably by placing it in suspension in tetrahydrofurane. It is hydrolyzed with precaution by adding a sodium sulfate solution.

Oxidation of the compound of formula VI is accomplished by means of pyridinium chlorochromate.

On this product, Schiff's base is obtained which is instantaneously reduced notably by solubilization under argon, preferably in ethanol, in the presence of triethylamine, methylamine hydrochloride, and titanium tetraisopropoxide, and then by adding sodium borohydride.

Deprotection of the ketone function in position 5 as well as the reaction with hydroxylamine is carried out under the conditions described earlier.

The compounds of formula II are known derivatives, described in the literature and are commercially accessible.

The object of the invention is further the use of a compound of formula I

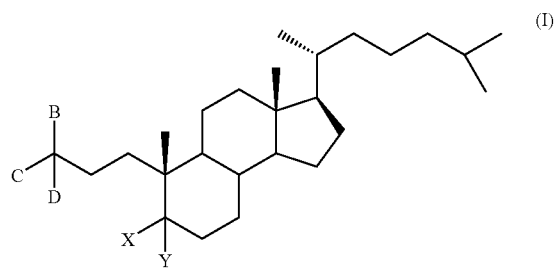

wherein

X represents together with Y a keto function, or X represents a hydroxyl and Y a hydrogen, or X and Y represent together an oxime (=NOH) or a methyloxime (=NHOMe), B represents a hydroxyl and C and D represent a hydrogen, or C and D represent 2 linear or branched alkyls with 1 to 4 carbon atoms, or C represents a hydrogen and D a linear or branched alkyl with 1 to 4 carbon atoms, or else B represents together with C a keto function and D a methyl, hydroxyl, or methylamine or else B and C represent a hydrogen and D a methylamine, or else, B and C together represent an oxime and D a methyl, or of one of its esters or one of its addition salts with pharmaceutically acceptable acids, or one of the addition salts of one of its esters with pharmaceutically acceptable acids, in order to obtain a neuroprotective drug, notably intended for treating neurodegenerative diseases such as for example Huntington's disease, neurodegenerative, hereditary or sporadic chronic diseases, neuronal lesions related to ageing, hereditary or lesional peripheral neuropathies, Charcot-Marie-Tooth's disease, diabetic neuropathies or those induced by anti-cancer treatments, traumas of the brain, of the peripheral nerves or those of the spinal cord, ischemias of the brain or of the spinal cord, hereditary, lesional degenerations, or those related to ageing of the sensory neurons of vision or degenerations of the optical nerve, hereditary, traumatic degenerations or those related to ageing of the sensory neurons of audition, lobar atrophies and vascular dementias, diseases and traumas related to degeneration of motoneurons, and more particularly spinal amyotrophies particularly infantile spinal amyotrophies, amyotrophic lateral sclerosis, multiple sclerosis and traumas of the spinal cord or of peripheral motor nerves.

Particularly, the object of the invention is the use of a compound of the above formula I, of salts or esters for obtaining a neuroprotective drug, notably intended for treating pathologies or traumas related to degeneration or death of neurons in mammals (generally patients) affected with such pathologies or traumas.

More particularly, the object of the invention is the use of a compound of formula I or of one of its salts or esters for obtaining a drug intended for treating infantile spinal amyotrophies and amyotrophic lateral scleroses.

Application of these drugs usually comprises the administration to these mammals of a therapeutically effective amount of a compound of formula I or of one of its esters, and notably of 3,5-seco-4-nor-cholestan-5-one oxime-3-ol, in particular for increasing survival of the neurons or promoting axonal growth. The object of the invention is just as well a method for treating the aforementioned diseases, notably neurodegenerative diseases, and notably a method for treating pathologies or traumas related to the degeneration or death of the neurons in mammals (generally patients) affected with such pathologies or traumas, comprising the administration to these mammals of a therapeutically effective amount of 3,5-seco-4-nor-cholestan-5-one oxime-3-ol, in particular for increasing survival of the neurons or promoting axonal growth.

Further, the object of the invention is a method for treating one of the affections described above and notably pathologies or traumas related to degeneration or death of motoneurons in mammals (generally patients) affected with such pathologies or traumas, comprising the administration to these mammals of a therapeutically effective amount of a compound of formula I or of one of its salts or esters, in particular for increasing the survival of neurons. More specifically, the pathologies related to degeneration or to death of motoneurons are amyotrophic lateral sclerosis or infantile spinal amyotrophies.

The object of the invention is just making available novel derivatives of 4-cholesten-3-one as well as derivatives of 4-cholesten-3-one other than those which may have been described in the state of the art. Those described in the literature are therefore excluded.

The preferential conditions described above for applying drugs of formula I are also applied to other objects of the invention targeted above, notably to the compositions, novel derivatives, uses and treatment methods, and vice versa.

The examples which follow illustrate the present application.

The retention times hereafter are expressed in minutes and hundredths of minutes.

The liquid chromatography method used for all the products is the following:
Column: Macherey-Nagel–Nucleosil® 300-6 C4–150× 4.6 mm
Gradient: water (+0.05% of trifluoroacetic acid)/acetonitrile (+0.05% of trifluoroacetic acid)
t=0 min: 60% acetonitrile, 40% $H_2O$
t=6 min: 100% acetonitrile, 0% $H_2O$
t=11 min: 100% acetonitrile, 0% $H_2O$
t=13 min: 60% acetonitrile, 40% $H_2O$
t=15 min: 60% acetonitrile, 40% $H_2O$.
The ionization conditions for the mass spectrometer are:
Temperature of the source: 250° C.
Cone voltage: 50 V
Capillary voltage: 3 kV
Rf lens: 0.3 V

EXAMPLE 1

3,5-seco-4-nor-cholestan-5-one oxime-3-methyl-amide

Stage A:
In a first phase, 250 mg of 3,5-seco-4-nor-cholestan-5-one oxime-3-oic acid, 38 mg of methylamine hydrochloride, 250 mg of EDCI, 100 mg of DMAP and 2,5 mL of dichloromethane are introduced into a flask. The solution is stirred for 24 hrs at room temperature and the reaction medium is then diluted by adding dichloromethane and washed with a 10% sodium bicarbonate solution. The organic phase is dried on magnesium sulfate and then concentrated under reduced pressure. The obtained residue is purified by flash chromatography (95/5 $CH_2Cl_2$/MeOH). 176 mg of 3,5-seco-4-nor-cholestan-5-one 3-methylamide are recovered with a yield of 68%.
Analysis
$^1$H-NMR ($CDCl_3$): in agreement
Retention time: 4 minutes 42 hundredths
Detected peaks in mass spectrometry: $[M+H]^+=418$; $[2M+H]^+=835$ Stage B:
Next, 50 mg of 3,5-seco-4-nor-cholestan-5-one 3-methylamide, 50 mg of hydroxylamine hydrochloride in 1 mL of pyridine are introduced into a flask. Stirring is performed for 16 hrs at room temperature and the reaction medium is then concentrated under reduced pressure. The obtained residue is taken up in a $CH_2Cl_2$/$H_2O$ mixture; the organic phase is separated, washed with water, dried on anhydrous sodium sulfate and concentrated under reduced pressure. 40.6 mg of 3,5-seco-4-nor-cholestan-5-one oxime-3-methylamide are recovered with a yield of 78%.
Analysis
$^1$H-NMR ($CDCl_3$): in agreement
Retention time: 3 minutes 70 hundredths
Detected peaks in mass spectrometry: $[M+H]^+=433$; $[2M+H]^+=865$

EXAMPLE 2

3,5-seco-4-nor-cholestan-5-one-3-dimethyl alcohol

Stage A:
10.5 g of 3,5-seco-4-nor-cholestan-5-one-3-oic acid in 378 mL of methanol and 146 mL of dichloromethane are solubilized in a flask. The mixture is cooled to 0° C. and 5.7 mL of thionyl chloride are added dropwise. The mixture is then stirred for 2 hrs at room temperature. The reaction medium is concentrated under reduced pressure, co-evaporated with toluene and then with dichloromethane. 10.3 g of 3,5-seco-4-nor-cholestan-5-one-3-methyl ester are obtained with a yield of 94%. The product is used as such without any purification.
$^1$H-NMR ($CDCl_3$): in agreement
Retention time: 4 minutes 69 hundredths
Detected peaks in mass spectrometry: $[M+H]^+=419$; $[2M+H]^+=785$ Stage B: 3,5-seco-4-nor-cholestane-5,5(ethylene dioxy)-3-methyl ester
9.62 g of 3,5-seco-4-nor-cholestan-5-one-3-methyl ester in 25 mL of trimethyl orthoformate and 53 mL of ethylene glycol are put into solution in a flask. 400 mg (2.3 mmol) of anhydrous p-toluene-sulfonic acid are then added and the mixture is stirred for 1 night at room temperature. Ethyl acetate is added to the reaction medium; washing is performed with a 10% sodium hydrogen carbonate solution. The organic phase is separated, dried on anhydrous magnesium sulfate and concentrated under reduced pressure. 9.95 g of 3,5-seco-4-nor-cholestane-5,5(ethylene dioxy)-3-methyl ester are obtained with a yield of 93%. The product is used as such without any purification.

$^1$H-NMR (CDCl$_3$): in agreement

Retention time: 5 minutes 76 hundredths

Detected peak in mass spectrometry: [M+H]$^+$=463

Stage C:

300 mg of 3,5-seco-4-nor-cholestane-5,5-ethylene dioxy)-3-methyl ester are solubilized in 5 mL of anhydrous THF. The medium is cooled to −45° C. and then 1.36 mL of 1.6M methyl lithium solution in ether is added dropwise. After 30 min of stirring at −45° C., a few drops of methanol are added to the reaction medium and the latter is brought back to room temperature. It is taken up in 20 mL of diethyl ether and washed with a sodium bicarbonate saturated solution and then with a sodium chloride saturated solution. The organic phase is dried on the magnesium sulfate and then concentrated under reduced pressure. 295 mg of 3,5-seco-4-nor-cholestane-5,5(ethylene dioxy)-3-dimethyl alcohol (MW=462) are obtained with a yield of 98%.

Retention time: 5 minutes 56 hundredths

Detected peak in mass spectrometry: [M−(CH$_2$OH—CH$_2$OH+H$_2$O)+H]$^+$=401

Stage D:

6 mL of a 1/1 water/acetic acid mixture and 295 mg of 3,5-seco-4-nor-cholestane-5,5(ethylene dioxy)-3-dimethyl alcohol are added into a flask; the mixture is heated to reflux for 1 hr 30 min. After cooling, the reaction medium is diluted with ethyl acetate, washed with a sodium chloride saturated solution, and then with a sodium bicarbonate saturated solution. Finally, the organic phase is dried on magnesium sulfate and concentrated under reduced pressure. The obtained raw product is purified by flash chromatography (8/2 petroleum ether/ethyl acetate). 180 mg of 3,5-seco-4-nor-cholestan-5-one-3-dimethyl alcohol are obtained with a yield of 68%.

$^1$H-NMR (CDCl$_3$): in agreement

Retention time: 5 minutes 08 hundredths

Detected peaks in mass spectrometry: [M+H]$^+$=419; [M−H$_2$O+H]$^+$=401; [2M+H]$^+$=837

EXAMPLE 3

3,5-seco-4-nor-cholestan-5-one oxime-3-dimethyl alcohol 1 g of the compound of Example 2, 1 g of hydroxylamine hydrochloride in 53 mL of pyridine and a few mL of dichloromethane for solubilizing the ketone are introduced into a flask. The mixture is stirred for 16 hrs at room temperature and the reaction medium is then concentrated under reduced pressure. The obtained residue is taken up in a CH$_2$Cl$_2$/H$_2$O mixture; the organic phase is separated, washed with water, dried on anhydrous sodium sulfate and concentrated under reduced pressure. 814 mg of 3,5-seco-4-nor-cholestan-5-one oxime-3-dimethyl alcohol are recovered with a yield of 78%.

$^1$H-NMR (CDCl$_3$): in agreement

Retention time: 5 minutes 09 hundredths

Detected peaks in mass spectrometry: [M+H]$^+$=434; [2M+H]$^+$=867

EXAMPLE 4

3,5-seco-4-nor-cholestan-5-one oxime-3-methyl alcohol

Stage A:

2 g of 3,5-seco-4-nor-cholestane-5,5(ethylene dioxy)-3-methyl ester in 26 mL of dioxane are placed in a flask. 8.6 mL of a 1N soda solution are added. The reaction medium is heated to reflux for 1 hr 30 min and dioxane is evaporated under reduced pressure. The obtained solution is acidified by adding a 1N hydrochloric acid solution up to pH=1 and extracted twice with toluene. The organic phases are collected, dried on anhydrous magnesium sulfate and concentrated under reduced pressure. 1.92 g of 3,5-seco-4-nor-cholestane-5,5(ethylene dioxy)-3-oic acid are recovered with a yield of 99%, which is used without any further treatment in the following step.

Stage B:

1.9 g of 3,5-seco-4-nor-cholestane-5,5(ethylene dioxy)-3-oic acid in 30 mL of dichloromethane are placed in a flask. To this solution, 1.06 g of EDCI, 743 mg of HOBT, 537 mg of N,O-dimethylhydroxylamine hydrochloride are added, and then dropwise 1.37 mL of triethylamine. The mixture is stirred at room temperature for 16 hrs. A mixture CH$_2$Cl$_2$/H$_2$O is added to the reaction medium and the latter is extracted three times with dichloromethane. The organic phases are collected, dried on anhydrous magnesium sulfate and concentrated under reduced pressure. The obtained residue is purified by flash chromatography (8/2 CH$_2$Cl$_2$/ethyl acetate). 1.46 g of 3,5-seco-4-nor-cholestane-5,5(ethylene dioxy)-3-(N,N-methoxy-methyl)amide are recovered with a yield of 70%.

$^1$H-NMR (CDCl$_3$): in agreement

Retention time: 5 minutes 31 hundredths

Detected peak in mass spectrometry: [M+H]$^+$=492

Stage C:

1.4 g of 3,5-seco-4-nor-cholestane-5,5(ethylene dioxy)-3-(N,N-methoxy-methyl)amide in 20 mL of anhydrous tetrahydrofurane are introduced into a flask under argon and cooled to 0° C. 3.38 mL of 1.6M methyl lithium solution in ether is then added dropwise. The reaction medium is stirred for 3 hrs 40 min at 0° C. and then a solution of 0.72 mL of concentrated hydrochloric acid in 7.28 mL of water is added dropwise. The tetrahydrofurane is evaporated under reduced pressure; the obtained aqueous solution is alcalinized by adding 1N soda up to pH=10. The solution is extracted with diethyl ether; the organic phases are collected, dried on anhydrous magnesium sulfate and concentrated under reduced pressure. The obtained residue is purified by flash chromatography (9/1 petroleum ether/ethyl acetate). 930 mg of 3,5-seco-4-nor-cholestane-5,5(ethylene dioxy)-3-methylketone are recovered with a yield of 73%.

$^1$H-NMR (CDCl$_3$): in agreement

Retention time: 5 minutes 65 hundredths

Detected peak in mass spectrometry: [M+H]$^+$=403

Stage D:

119 mg of 3,5-seco-4-nor-cholestane-5,5(ethylene dioxy)-3-methylketone from stage C in 1.5 mL of methanol are placed in a flask. The mixture is cooled to 0° C. and 10 mg of sodium borohydride are added. The reaction medium is stirred at 0° C. for 1 hr and then concentrated under reduced pressure. The residue is taken up in water and extracted with dichloromethane. The organic phase is dried on magnesium sulfate and concentrated under reduced pressure. 94 mg of 3,5-seco-4-nor-cholestane-5,5(ethylene dioxy)-3-methyl alcohol are recovered with a yield of 78%, this product is used as such.

$^1$H-NMR (CDCl$_3$): in agreement
Retention time: 5 minutes 22 hundredths
Detected peak in mass spectrometry: [M+H]$^+$=387

Stage E:
One operates as in stage D of Example 2 for deprotecting the ketone in position 5.

Stage F:
121 mg of 3,5-seco-4-nor-cholestan-5-one-3-methyl alcohol, 1.5 mL of pyridine and 121 mg of hydroxylamine hydrochloride are introduced into a flask. The solution is stirred for 2 days at room temperature. The reaction medium is concentrated under reduced pressure, taken up in water and extracted with dichloromethane. The organic phase is then washed with water, and then dried on magnesium sulfate and concentrated under reduced pressure. The thereby obtained product is purified by flash chromatography (9/1 petroleum ether/ethyl acetate). 66 mg of 3,5-seco-4-nor-cholestan-5-one oxime-3-methyl alcohol are obtained with a yield of 53%.

$^1$H-NMR (CDCl$_3$): in agreement
Retention time: 4 minutes 91 hundredths
Detected peak in mass spectrometry: [M+H]$^+$=420

EXAMPLE 5

3,5-seco-4-nor-cholestan-5-one oxime-3-methyl-amine

Stage A:
615 mg of LiAlH$_4$ are suspended in 57 mL of THF in a flask. The mixture is cooled to 0° C. and a solution of 3.0 g of 3,5-seco-4-nor-cholestane-5,5(ethylene dioxy)-3-methyl ester is added dropwise in 57 mL of tetrahydrofurane. The mixture is then stirred at 0° C. for 5 hrs. Hydrolysis is performed with precaution by adding a sodium sulfate solution; the obtained white solution is stirred for 30 min and then filtered. The filtrate is concentrated under reduced pressure and taken up in water, extracted with ethyl acetate. The organic phase is dried on magnesium sulfate and then concentrated under reduced pressure. 2.55 g of 3,5-seco-4-nor-cholestane-5,5(ethylene dioxy)-3-ol are obtained with a yield of 85%, this product is used as such.

$^1$H-NMR (CDCl$_3$): in agreement
Retention time: 4 minutes 82 hundredths
Detected peak in mass spectrometry: [M-(CH$_2$OH—CH$_2$OH+H$_2$O)+H]$^+$=373

Stage B:
476 mg of 3,5-seco-4-nor-cholestane-5,5(ethylene dioxy)-3-ol in 7 mL of dichloromethane is solubilized in a flask under argon, and 189 mg of neutral alumina and 399 mg of pyridinium chlorochromate are then added; the mixture is stirred at room temperature for 3 hrs 30 min. The reaction medium is filtered on Celite®; the filtrate is concentrated under reduced pressure. The obtained residue is purified by flash chromatography (9/1 and then 8/2 toluene/ethyl acetate). 328 mg of 3,5-seco-4-nor-cholestane-5,5(ethylene dioxy)-3-al are obtained with a yield of 69%.

Retention time: 5 minutes 57 hundredths
Detected peak in mass spectrometry: [M+H]$^+$=433

Stage C:
323 mg of 3,5-seco-4-nor-cholestane-5,5(ethylene dioxy)-3-al in 3 mL of ethanol are solubilized in a flask under argon, and 209 µL of triethylamine, 100 mg of methylamine hydrochloride and 444 µL of titanium tetraisopropoxide are then added. The reaction medium is stirred for 6 hrs at room temperature, and 42.5 mg of sodium borohydride are added. The mixture is stirred for 16 hrs at room temperature. The reaction medium is filtered and washed with dichloromethane. The filtrate is dried on magnesium sulfate and concentrated under reduced pressure. The obtained residue is purified by flash chromatography (9/1 to 5/5 dichloromethane/methanol). 84 mg of 3,5-seco-4-nor-cholestane-5,5(ethylene dioxy)-oxime-3-methylamine are obtained with a yield of 25%.

$^1$H-NMR (CDCl$_3$): in agreement
Retention time: 3 minutes 93 hundredths
Detected peak in mass spectrometry: [M+H]$^+$=448

Stage D:
50 mg of 3,5-seco-4-nor-cholestane-5,5(ethylene dioxy)-3-methylamine and 976 µL of a 1/1 water/acetic acid mixture are introduced into a flask. The mixture is refluxed for 6 hrs. After cooling, the reaction medium is diluted with ethyl acetate and washed with a sodium chloride saturated solution and then with a 5% sodium bicarbonate solution. The organic phase is dried on magnesium sulfate and concentrated under reduced pressure. The obtained product is purified by flash chromatography (95/5 dichloromethane/methanol); 5 mg of 3,5-seco-4-nor-cholestan-5-one-3-methylamine are obtained with a yield of 11%.

$^1$H-NMR (CDCl$_3$): in agreement
Retention time: 3 minutes 68 hundredths
Detected peak in mass spectrometry: [M+H]$^+$=404

Stage E:
5 mg of 3,5-seco-4-nor-cholestan-5-one-3-methylamine, 5 mg of hydroxylamine hydrochloride and 287 µL of pyridine are introduced into a flask. The mixture is stirred for 16 hrs at room temperature. It is then taken up into dichloromethane and washed with water. The organic phase is dried on magnesium sulfate and concentrated under reduced pressure. 5 mg of 3,5-seco-4-nor-cholestan-5-one oxime-3-methylamine are obtained with a yield of 91%.

Retention time: 3 minutes 66 hundredths
Detected peak in mass spectrometry: [M+H]$^+$=419

EXAMPLE 6

3,5-seco-4-nor-cholestan-5-one methyloxime-3-ol 20 mg of 3,5-seco-4-nor-cholestan-5-one-3-ol, 20 mg of O-methylhydroxylamine hydrochloride in 1 mL of pyridine are introduced into a flask. The mixture is stirred for 16 hrs at room temperature and 10 mg of O-methylhydroxylamine hydrochloride are again added. The mixture is again stirred for 16 hrs at room temperature and then the reaction medium is concentrated under reduced pressure. The obtained residue is taken up in a CH$_2$Cl$_2$/H$_2$O mixture; the organic phase is separated, washed with water, dried on anhydrous magnesium sulfate and concentrated under reduced pressure. 18 mg of yellow oil which is purified by flash chromatography (9/1 petroleum ether/ethyl acetate) are obtained, 5.8 mg of 3,5-seco-4-nor-cholestan-5-one methyloxime-3-ol are recovered with a yield of 27%.

Analysis
$^1$H-NMR (CDCl$_3$): in agreement
Retention time: 5 minutes 50 hundredths
Detected peak in mass spectrometry: [M+H]$^+$=420

EXAMPLE 7

3,5-seco-4-nor-cholestan-5-one carboxymethyl-oxime-3-ol 52 mg of ketone, 25 mg of hemi-hydrochloride of carboxymethoxylamine in 0.5 mL of pyridine are introduced into a flask. The mixture is stirred for 2 days at room temperature and the reaction medium is concentrated under reduced pressure. The obtained residue is taken up in a $CH_2Cl_2/H_2O$ mixture; the organic phase is separated, washed with water and then with a 2% hydrochloric acid solution, dried on anhydrous sodium sulfate and concentrated under reduced pressure. The obtained residue is purified by flash chromatography (8/2 petroleum ether/ethyl acetate). 24 mg are obtained with a yield of 39% for the carboxymethyloxime.

Analysis
$^1$H-NMR ($CDCl_3$): in agreement
Retention time: 4 minutes 40 hundredths
Detected peaks in mass spectrometry: $[M+H]^+=464$; $[2M+H]^+=927$

EXAMPLE 8

| A suspension was prepared which is described by the formulation | |
|---|---|
| 3,5-seco-4-nor-cholestan-5-one oxime-3-ol | 20 mg per mL |
| excipient: | oily emulsion |

EXAMPLE 9

| A dry form was prepared described by the formulation | |
|---|---|
| 3,5-seco-4-nor-cholestan-5-one oxime-3-N,N-dimethylglycine ester hydrochloride | 250 mg |
| excipient: qsp a capsule completed to | 750 mg |

EXAMPLE 10

Prodrug of 3,5-seco-4-nor-cholestan-5-one oxime-3-ol 3,5-seco-4-nor-cholestan-5-one oxime-3-N,N-dimethylglycine ester 509 mg of 3,5-seco-4-nor-cholestan-5-one-3-ol, 182 mg of N,N-dimethylglycine hydrochloride, 275 mg of EDCI and 207 mg of DMAP in 10-15 mL of dichloromethane are placed in a flask. The mixture is stirred at room temperature for 16 hrs. A 5% sodium bicarbonate solution is added to the reaction medium and the latter is extracted with dichloromethane. The organic phases are collected, dried on anhydrous sodium sulfate and concentrated under reduced pressure. The obtained residue is purified by flash chromatography (8/2 toluene/ethyl acetate). 488 mg are recovered with a yield of 78%.

Analysis
$^1$H-NMR ($CDCl_3$): in agreement
Retention time: 3 minutes 77 hundredths
Detected peak in mass spectrometry: $[M+H]^+=476$ The product is then entered into the following reaction:
488 mg of the obtained product and 488 mg of hydroxylamine hydrochloride in 23 mL of pyridine are introduced into a flask. The mixture is stirred for 16 hrs at room temperature and then the reaction medium is taken up in a $CH_2Cl_2/H_2O$ mixture; the organic phase is separated, washed with water, dried on anhydrous sodium sulfate and concentrated under reduced pressure. 378 mg of the oxime are recovered with a yield of 75%. The product is then salified in the presence of an ether solution acidified with a HCl solution, in order to obtain the product as a hydrochloride.

Analysis
$^1$H-NMR ($CDCl_3$): in agreement
Retention time: 3 minutes 43 hundredths
Detected peak in mass spectrometry: $[M+H]^+=491$

EXAMPLE 11

Prodrug of 3,5-seco-4-nor-cholestan-5-one oxime-3-ol 3,5-seco-4-nor-cholestan-5-one oxime-3-(4-methyl-1-piperazine) propanoate ester 264 mg of 3,5-seco-4-nor-cholestan-5-one-3-ol, 121 mg of 4-methyl-1-piperazine-propanoic acid as a lithium salt, 1,425 mg of EDCI and 106 mg of DMAP in 2-3 mL of dichloromethane are placed in a flask. The mixture is stirred at room temperature for 1 night. Water is added to the reaction medium and the latter is extracted with dichloromethane. The organic phases are collected, dried on anhydrous sodium sulfate and concentrated under reduced pressure. The obtained residue is purified by flash chromatography (98/2 toluene/ethyl acetate). 54 mg of the desired product are recovered with a yield of 15%.

Analysis
$^1$H-NMR ($CDCl_3$): in agreement
Retention time: 3 minutes 66 hundredths
Detected peak in mass spectrometry: $[M+H]^+=545$ The product is then entered into the following reaction:
30 mg of the obtained product and 30 mg of hydroxylamine hydrochloride in 1.2 mL of pyridine are introduced into a flask. The mixture is stirred for 5 hrs 30 min at room temperature and then the reaction medium is taken up in a $CH_2Cl_2/H_2O$ mixture; the organic phase is separated, washed with water, dried on anhydrous sodium sulfate and concentrated under reduced pressure. 19 mg of the oxime are recovered with a yield of 13%.

Analysis
$^1$H-NMR ($CDCl_3$): in agreement
Retention time: 3 minutes 66 hundredths
Detected peak in mass spectrometry: $[M+H]^+=560$ The product is then salified in the presence of an ether solution acidified with an aqueous solution of hydrochloric acid, in order to obtain the product as a dihydrochloride.

| Compound no. | |
|---|---|
| 1 | Compound of Example 1 |
| 2 | Compound of Example 4 |
| 3 | Compound of Example 3 |
| 4 | Compound of Example 4 |
| 5 | Compound of Example 5 |
| 6 | Compound of Example 6 |
| 7 | Compound of Example 7 |
| 8 | 3,5-seco-4-nor-cholestan-5-one oxime-3-oic acid described in Azasteroidal alkaloids. Synthesis of A-nor-B-homo-5-azacholestane. Rodewald, W. J.; Wicha, J. Univ. Warsaw, Bulletin of the Polish Academy of Sciences, Chemical Science Series (1963), 11(8), 437-41. |
| 9 | 3,5-seco-4-nor-cholestane-3,5-diol described in US-A 2,883,424 |

-continued

| Compound no. | |
|---|---|
| 10 | 3,5-seco-4-nor-cholestan-5-one-3-ol described in Azasteroidal alkaloids. Synthesis of A-nor-B-homo-5-azacholestane. Rodewald, W. J.; Wicha, J. Univ. Warsaw, Bulletin of the Polish Academy of Sciences, Chemical Science Series (1963), 11(8), 437-41. |
| 11 | 3,5-seco-4-nor-cholestan-5-one oxime-3-ol described in Azasteroidal alkaloids. Synthesis of A-nor-B-homo-5-azacholestane. Rodewald, W. J.; Wicha, J. Univ. Warsaw, Bulletin of the Polish Academy of Sciences, Chemical Science Series (1963), 11(8), 437-41. |
| 12 | 3,5-seco-4-nor-cholestan-5-one oxime-3-one oxime described in Unusual reactions of steroidal and non-steroidal 1,5-dioximes. Stereochemistry and mechanism of formation of N-hydroxypiperidine analogs. Pradhan, Suresh K.; Akamanchi, Krishnacharya G.; Divakaran, Pulukkunatt P.; Pradhan, Prakash M. Dep. Chem. Technol. Univ. Bombay, Bombay India. Heterocycles (1989), 28(2), 813-39 |
| 13 | 3,5-seco-4-nor-cholestan-5-one-3-methyl ketone described in Oxidation of cyclic hemiacetals into diketones: final steps in the conversion of a triterpenoid ring A into a steroidal enone by a new short route. Uusvuori, Raimo; Hase, Tapio A. Dep. Cham., Helsinki Univ. Technol. Espoo, Finland. Synthetic communications (1982), 12(14), 1081-8. |
| 14 | 3,5-seco-4-nor-cholestan-5-one-3-oic acid described in Azasteroidal alkaloids. Synthesis of A-nor-B-homo-5-azacholestane. Rodewald, W. J.; Wicha, J. Univ. Warsaw, Bulletin of the Polish Academy of Sciences, Chemical Science Series (1963), 11(8), 437-41. |

1. Effects of the Compounds of Formula I on Survival of Motoneurons

In order to demonstrate the neuroprotective action of the compounds of formula I, the applicant investigated their activity on an in vitro model of trophic deprivation of rat motoneurons. Useful reference may be made to the WO 0142784 Patent Application of the applicant on the cultivation of spinal cord motoneurons.

The spinal cord of rat E14 embryos is dissected and the ventral portion is dissociated by trituration after trypsination. The motoneurons are separated from the other spinal cells by a known method (Camu et al., 1993, Purification of spinal motoneurons from chicken and rat embryos by immunopanning. in "Immunoselection Strategies for Neural cell culture", Neuroprotocols: A companion to Methods in Neurosciences 2, 191-199; Henderson et al., 1993. Neutrophins promote motor neuron survival and are present in embryonic limb bud. Nature 363 (6426): 266-70). The cells are centrifuged on a density gradient. Motoneurons are enriched in the fraction of large cells (the less dense cells). The cells of this fraction are incubated with an anti-p75 antibody, a surface antigen present on motoneurons. Secondary antibodies coupled with magnetic beads are added and the mixture of cells is passed through a column in a magnet (Arce et al., 1999). Only the motoneurons are retained: their purity is of the order of 90%.

The motoneurons are sown with low density in culture wells on a substrate of polyornithine-laminin in a neurobasal medium supplemented according to Raoul et al., 1999, Programmed cell death of embryonic motoneurons triggered through the Fas death receptor. J. Cell. Biol. 147(5): 1049-62. Negative controls (absence of trophic factors) and positive controls (in the presence of BDNF (Brain-Derived Neurotrophic Factor) at 1 ng/mL, GDNF (Glial-Derived Neurotrophic Factor) at 1 ng/mL, and CNTF (Ciliary Neurotrophic Factor) at 10 ng/mL, marketed by the US company PEPROTECH, Inc. and the Sigma-Aldrich company), are included in each series.

The compounds to be tested are added 60 minutes after sowing and the cultures are maintained at 37° C. under 5% $CO_2$ for 3 days.

The motoneurons have a spontaneous tendency of dying in the absence of neurotrophic factors (Pettmann and Henderson, 1998, Neuronal cell death. Neuron 20(4): 633-47). After 3 days, survival is evaluated by measuring fluorescence after incubating the cells in the presence of calcein which becomes fluorescent in living cells.

After 3 days in culture at 37° C., under 5% $CO_2$ and in saturating humidity, up to 50% of the initially sown motoneurons survive in the medium supplemented with neurotrophic factors, while less than 15% of the motoneurons survive in a basal medium alone.

The activity of the compounds to be tested was evaluated by their capability of preventing death of motoneurons when they are added to the neurobasal medium as compared with survival of motoneurons in a medium supplemented with neurotrophic factors.

The compounds of formula I according to the invention demonstrated activity at a concentration capable of allowing a better survival rate of the motoneurons in the basal medium. This survival rate is expressed by a number, the ratio. If the ratio is greater than 0, the effect of the compounds is positive on the survival of the motoneurons.

The obtained results are the following:

| Compound No. | Concentration in μM | Ratio |
|---|---|---|
| 1 | 3 | 0.4 |
| 2 | 3 | 0.5 |
| 3 | 3 | 0.7 |
| 4 | 3 | 0.5 |
| 5 | 3 | 0.3 |
| 6 | 3 | 0.4 |
| 7 | 3 | 0.4 |
| 8 | 3 | 0.4 |
| 9 | 3 | 0.4 |
| 10 | 3 | 0.6 |
| 11 | 3 | 0.8 |
| 12 | 3 | 0.7 |
| 13 | 3 | 0.7 |
| 14 | 10 | 0.4 |

By virtue of their trophic effect on spinal motoneurons, the compounds of formula I according to the invention therefore prove to be useful as a drug, notably in treating amyotrophies, in particular in treating amyotrophic lateral sclerosis or infantile spinal amyotrophies, and in treating traumas of the spinal cord.

2. Effects of the Compounds of Formula I on Neuroprotection

An axotomy of the facial nerve is carried out on newborn rats aged from 2-3 days. The animals receive compounds, nos. 11, 3 and 4, 4 hrs before unilateral section of the nerve and then daily for 5 days subcutaneously. Seven days after section of the nerve, the animals are anaesthetized, and then fixed by intra-cardial infusion of paraformaldehyde. The brain is then taken out, included in paraffin. Histological analysis of serial 7 μm cuts of the facial nucleus, stained with cresyl violet, allows the number of motoneurons on the intact side as well on the sectioned nerve side to be counted (Casanovas et al., Prevention by lamotrigine, MK-801 and N omega-nitro-L-arginine methyl ester of motoneuron cell death after neonatal axotomy, Neuroscience, 1996, 71, 313-325).

The obtained results are the following:

Survival of the motoneurons of the facial nucleus in axotomized newborn rats and treated orally with compounds no. 11, 3 and 4 give an increase of up to 40% at a dose between 3 and 30 mg/kg as compared with non-sectioned nerve, an increase of up to 25% at a dose of 10 mg/kg, an increase of up to 30% at a dose of 30 mg/kg, respectively.

Toxicological Study

Administrations in mice, in particular of compounds 11, 3 and 4, via the intra-peritoneal route, at a dose of 30 mg/kg/day, by treatment with daily administration which may last up to 14 days, did not show any significant toxicity.

The invention claimed is:

1. A compound which is (a) a compound described by formula I

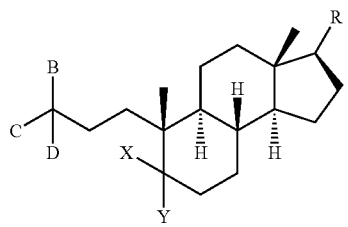

(I)

wherein
(i) X represents together with Y and the carbon to which they are attached a keto function, or
(ii) X represents a hydroxyl group and Y a hydrogen, or
(iii) X and Y and the carbon to which they are attached together represent an oxime group (>C=NOH) or
(iv) X and Y and the carbon to which they are attached together represent a methyloxime group (>C=NOMe), and wherein
(1) B represents a hydroxyl group and C and D represent a hydrogen, or
(2) B represents a hydroxyl group and C and D represent linear or branched alkyls with 1 to 4 carbon atoms, or
(3) B represents a hydroxyl group and C represents a hydrogen and D a linear or branched alkyl with 1 to 4 carbon atoms, or
(4) B represents together with C and the carbon to which they are attached a keto function and D a methyl, hydroxyl or methylamine or
(5) B and C represent a hydrogen and D a methylamine, or
(6) B and C and the carbon to which they are attached together represent an oxime and D a methyl, and wherein R represents a linear or branched alkyl with 1 to 10 carbon atoms;
or which compound is (b) an addition salt of the compound of (a) with a pharmaceutically acceptable acid, or an ester of (a), or an addition salt of said ester with a pharmaceutically acceptable acid;
with the provisos that
if (i) applies, that (2), (3), (5) or (6) apply,
if (ii) applies, that (4), (5) or (6) apply,
if (iii) applies, that (2), (3), or (5) apply, and
if (iv) applies, that (1), (2), (3), (5) or (6) apply.

2. A compound according to claim 1, characterized in that in formula I, R represents the radical

—CH(CH$_3$)—(CH$_2$)$_3$—CH(CH$_3$)$_2$.

3. A compound according to claim 1, which is (a) a compound selected from the group consisting of
3,5-seco-4-nor-cholestan-5-one oxime-3-methyl alcohol, and
3,5-seco-4-nor-cholestan-5-one oxime-3-dimethyl alcohol, or (b) an addition salt of (a) with a pharmaceutically acceptable acid or an ester of (a) or an addition salt of said ester with a pharmaceutically acceptable acid.

4. The compound of claim 1 wherein condition (5) applies.

5. The compound of claim 1 wherein
if (i) applies, (2), (3) or (5) apply;
if (ii) applies, (4) or (5) apply; and
if (iv) applies, (2), (3) or (5) apply.

6. The compound of claim 1 wherein (iii) applies.

7. A compound which is (a) a compound described by formula I

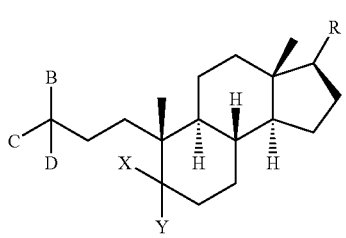

(I)

wherein
X and Y and the carbon to which they are connected represent together an oxime, B and C represent a hydrogen and D a methyl amine, or X represents together with Y and the carbon to which they are connected a keto function, B represents a hydroxyl radical, and C and D represent methyls, or X and Y and the carbon to which they are connected together represent an oxime, B represents a hydroxyl, and C and D represent methyls, or X and Y and the carbon to which they are connected together represent an oxime, B represents a hydroxyl, C represents a hydrogen and D represents a methyl, or X and Y and the carbon to which they are connected together represent the methyl oxime group, B represents hydroxyl and C and D represent hydrogens, or (b) an addition salt of the compound of (a) with a pharmaceutically acceptable acid, or an ester of (a), or an addition salt of the ester of (b) with a pharmaceutically acceptable acid R represents a linear or branched alkyl with 1 to 10 carbon atoms.

8. A pharmaceutical composition characterized in that it comprises (I) as an active ingredient, a compound which is (a) the compound of formula I,

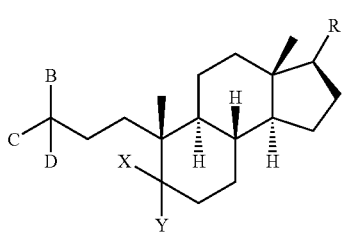

(I)

wherein
(i) X represents together with Y and the carbon to which they are attached a keto function, or (ii) X represents a hydroxyl group and Y a hydrogen, or (iii) X and Y and the carbon to which they are attached together represent an oxime group (>C=NOH) or (iv) X and Y and the carbon to which they are attached together represent a methyloxime group (>C=NOMe), and wherein
(1) B represents a hydroxyl group and C and D represent a hydrogen, or (2) B represents a hydroxyl group and C and D represent linear or branched alkyls with 1 to 4 carbon atoms, or (3) B represents a hydroxyl group and C represents a hydrogen and D a linear or branched alkyl with 1 to 4 carbon atoms, or (4) B represents together with C and the carbon to which they are attached a keto function and D a methyl, hydroxyl or methylamine or (5) B and C represent a hydrogen and D a methylamine, or (6) B and C and the carbon to which they are attached together represent an oxime and D a methyl,
and wherein R represents a linear or branched alkyl with 1 to 10 carbon atoms, or which compound is (b) an addition salt of the compound of (a) with a pharmaceutically acceptable acid, or an ester of (a), or an addition salt of said ester with a pharmaceutically acceptable acid;
and (II) one or more inert, pharmaceutically acceptable additional ingredients, wherein all ingredients of said pharmaceutical composition are pharmaceutically acceptable.

9. The composition of claim 8 wherein at least one inert, pharmaceutically acceptable ingredient is saline (sodium chloride).

10. The composition of claim 8 wherein said saline is physiological saline.

11. The composition of claim 8 wherein at least one inert, pharmaceutically acceptable ingredient is selected from the group consisting of methylcellulose, hydroxymethyl-cellulose, carboxymethylcellulse, cyclodextrins, polysorbate 80, mannitol, gelatin, lactose, vegetable or animal oils, and acacia.

12. The composition of claim 8 which is the form of a gel, tablet, suppository or capsule.

13. The composition of claim 8 which is in the form of an oily suspension.

14. The composition of claim 8 which is in the form of an injectable suspension.

15. The composition of claim 8 in unit dosage form.

16. A method for providing neuroprotection of neurons which comprises exposing neurons to a neuron-protective amount of a compound that is capable of protecting neurons, which compound is (a) a compound described by formula (I)

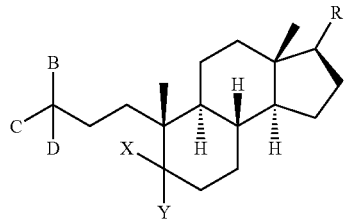

(I)

wherein
(i) X represents together with Y and the carbon to which they are attached a keto function, or (ii) X represents a hydroxyl group and Y a hydrogen, or (iii) X and Y and the carbon to which they are attached together represent an oxime group (>C=NOH) or (iv) X and Y and the carbon to which they are attached together represent a methyloxime group (>C=NOMe), and wherein
(1) B represents a hydroxyl group and C and D represent a hydrogen, or (2) B represents a hydroxyl group and C and D represent linear or branched alkyls with 1 to 4 carbon atoms, or (3) B represents a hydroxyl group and C represents a hydrogen and D a linear or branched alkyl with 1 to 4 carbon atoms, or (4) B represents together with C and the carbon to which they are attached a keto function and D a methyl, hydroxyl or methylamine or (5) B and C represent a hydrogen and D a methylamine, or (6) B and C and the carbon to which they are attached together represent an oxime and D a methyl,
and wherein R represents a linear or branched alkyl with 1 to 10 carbon atoms,
or which compound is (b) an addition salt of the compound of (a) with a pharmaceutically acceptable acid, or an ester of (a), or an addition salt of said ester with a pharmaceutically acceptable acid.

17. The method according to claim 16, characterized in that the compound of formula I is 3,5-seco-4-nor-cholestan-5-one oxime-3-ol, or one of its addition salts with pharmaceutically acceptable acids or one of its esters or one of the addition salts with pharmaceutically acceptable acids of said esters.

18. The method of claim 16 wherein the neurons are motoneurons, and the motoneurons are protected from degeneration or death.

19. The method of claim 18 wherein the protection occurs in a subject suffering from a neurodegenerative disease or pathology.

20. The method of claim 19 wherein the disease or pathology is a spinal muscular atrophy.

21. The method of claim 19 wherein the disease or pathology is an infantile spinal muscular atrophy.

22. The method of claim 19 wherein the disease or pathology is amyotrophic lateral sclerosis.

23. The method of claim 19 wherein the disease or pathology is multiple sclerosis.

24. The method of claim 16 wherein
if (i) applies, (1), (2) or (4) apply; and
if (ii) or (iv) applies, (1) applies.

25. The method of claim 16 wherein (iii) applies.

* * * * *